United States Patent [19]
Villard

[11] 4,149,536
[45] Apr. 17, 1979

[54] APPARATUS FOR THE APPLICATION OF A TREATING AGENT TO THE HUMAN BODY

[76] Inventor: Pierre Villard, Le Grand Lemps (Isère)

[21] Appl. No.: 770,229

[22] Filed: Feb. 18, 1977

[30] Foreign Application Priority Data

Feb. 19, 1976 [FR] France .............................. 76 05164

[51] Int. Cl.² ............................................ A61M 35/00
[52] U.S. Cl. .................................... 128/261; 128/365
[58] Field of Search .................. 128/261, 262, 65, 66, 128/371, 365–368, 369–373; 4/279

[56] References Cited

U.S. PATENT DOCUMENTS

| | | | |
|---|---|---|---|
| 1,637,423 | 8/1927 | Miller | 128/66 UX |
| 2,292,666 | 8/1942 | Schurtz | 128/366 |
| 3,885,557 | 5/1975 | Varea | 128/365 X |

Primary Examiner—Robert W. Michell
Assistant Examiner—Milford Juten
Attorney, Agent, or Firm—Karl F. Ross

[57] ABSTRACT

An apparatus for the application of a treating agent, e.g. paraffin, to the human body for slimming comprises a unit having a first receptacle containing the pure paraffin, a second receptacle for recovering and sterilizing the paraffin, and a third receptacle containing washing water, the unit being adapted to roll along a floor. Each of the receptacles is provided with a heater and the unit has a pump for recycling the liquids and a device for distributing the paraffin emulsion on the body of the subject.

7 Claims, 5 Drawing Figures

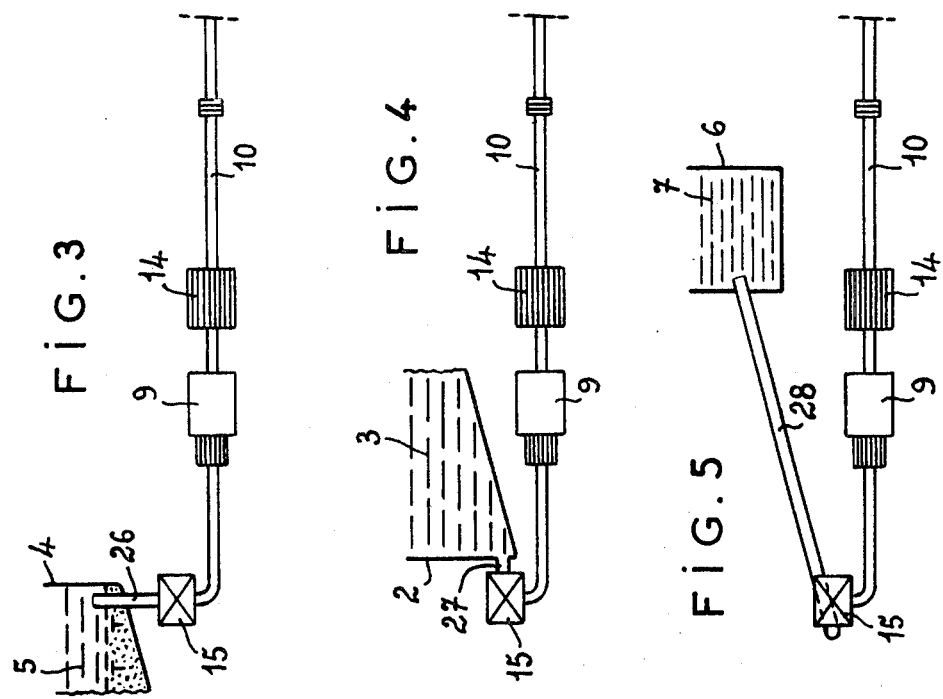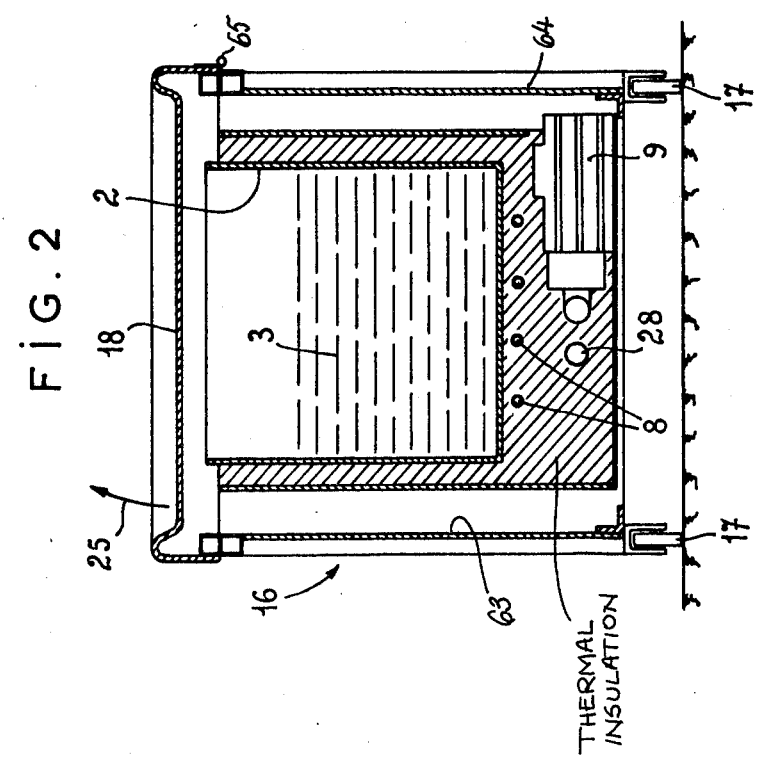

APPARATUS FOR THE APPLICATION OF A TREATING AGENT TO THE HUMAN BODY

FIELD OF THE INVENTION

The present invention relates to an apparatus for treating the human body and, more particularly, to an apparatus for applying paraffin to a subject in a slimming treatment or for applying a depilatory agent.

BACKGROUND OF THE INVENTION

In a slimming treatment (defattening) in actual use, the human body or a part thereof can be coated with paraffin at its melting point such that a sheath or layer of paraffin surrounds the body part to induce transpiration. More precisely, the paraffin has the effect of accelerating the organic combustion process in the subcutaneous and the subadipose cellular tissues of the skin and of eliminating wastes produced in the reaction. The increased metabolism of the tissues below the epidermis causes a loss of weight of the body part and a sloughing of dead skin.

In conventional techniques for practicing this process, the paraffin is heated to its melting point, usually emulsified, and applied to the skin by a brush. The paraffin layer is maintained in place for a variable period of the order of fifteen minutes to one hour and is then removed. This technique is time consuming and difficult, requiring fastidious practitioners and is annoying to the subject treated.

OBJECTS OF THE INVENTION

It is the principal object of the present invention to provide an improved apparatus for effecting a treatment of the human body which obviates the disadvantages of earlier systems for this purpose.

Another object of the invention is to provide an improved apparatus for coating the body of the subject with paraffin in a convenient and economical manner.

Still another object of the invention is to provide a single unit which can perform all the necessary functions relating to the coating of the human body with paraffin in a slimming treatment.

It is also an object of the invention to provide a compact, efficient and economical apparatus free from the disadvantages of earlier systems and adapted to carry out an effective treatment of the human body with a meltable substance, usually parafin.

SUMMARY OF THE INVENTION

These objects are attained, in accordance with the invention, in an apparatus which comprises, in combination and in a single mobile unit, a first reservoir or receptacle adapted to hold the pure paraffin, a second receptacle or reservoir adapted to recover and sterilize the used paraffin after treatment of the subject, and a third receptacle or reservoir holding washing water, each of these reservoirs being provided with heating means to maintain the water and the paraffin at the desired temperature levels. The apparatus is provided with pump means for recycling the liquids (circulating same), means for distribution of the paraffin preferably in a pulverized and emulsified form (e.g. as atomized particles) onto the body of the subject who can be recumbent upon a platform or bed during the treatment.

According to a feature of the invention, the apparatus comprises a four-way valve permitting communication between an inlet conduit and the liquid of the distributing means and one of the three reservoirs or receptacles mentioned previously. Preferably, the second reservoir or receptacle is formed as a decantation tank provided with a filter at its lower portion for separating the platform from the water and the detritus formed in the course of treatment. According to still another feature of the invention the distributing means comprises a flexible conduit formed at its end with a nozzle or spray gun for the platform.

BRIEF DESCRIPTION OF THE DRAWING

The above and other objects, features and advantages of the present invention will become more readily apparent from the following description, reference being made to the accompanying drawing in which:

FIG. 2 is a transverse cross section through a portion of the apparatus of FIG. 1; and FIGS. 3 through 5 are schematic illustrations of the mode of use of each of the three reservoirs or receptacles of the apparatus in the course of a slimming treatment.

SPECIFIC DESCRIPTION

Figure 1:
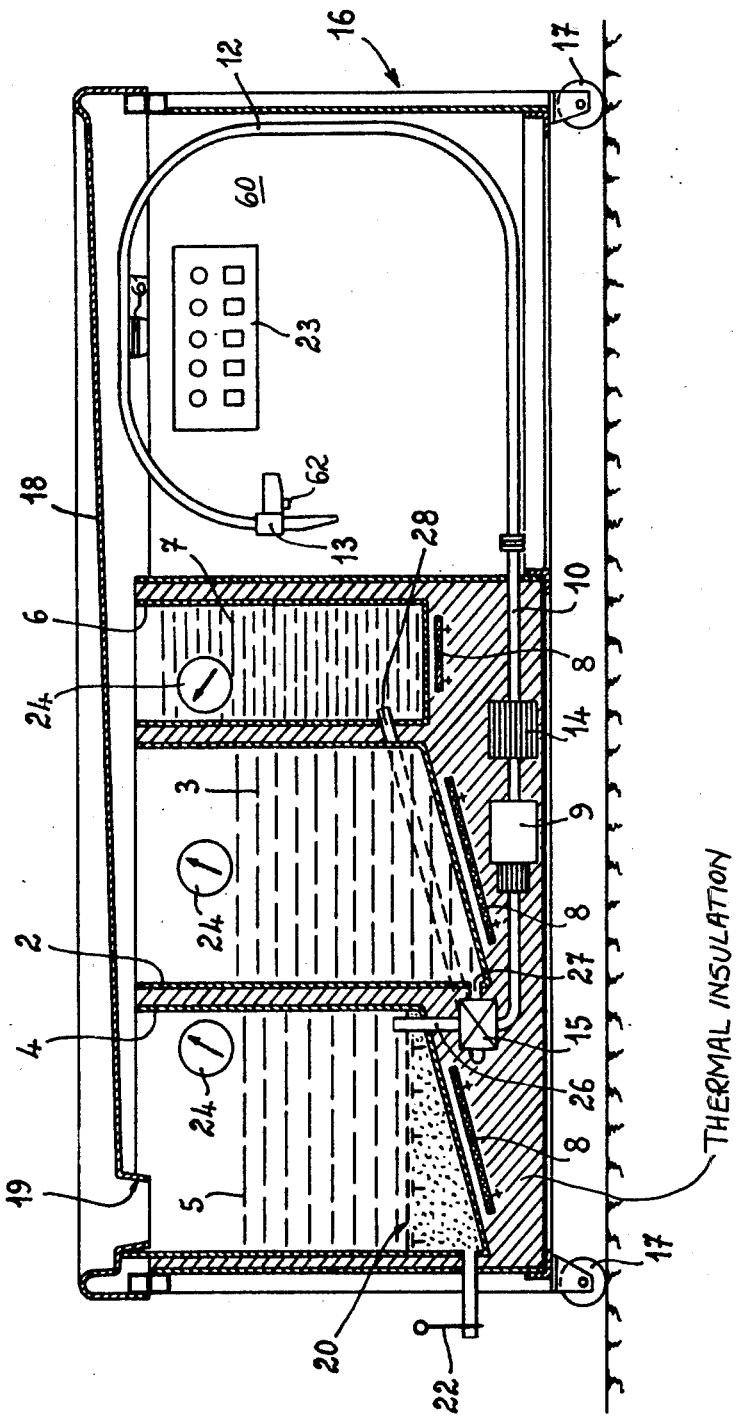
FIG. 1 is a diagrammatic elevational view, partially in longitudinal section, of an apparatus according to the invention.

The apparatus shown in FIGS. 1 and 2 comprise, on a common support, a first reservoir to be adapted to receive the pure paraffin shown in a liquid state 3. Adjacent the reservoir 2, and on one side thereof, is a second reservoir 4 adapted to hold recovered paraffin 5 for decantation to separate it from water and detritus, and to sterilize it for reuse. On the opposite side of the reservoir 2, there is a third reservoir 6 containing the washing water 7. Each of these reservoirs is provided at its bottom with heating means in the form of an electric resistance heater 8 adapted to maintain the paraffin in the reservoirs 2 and 4 and the water in the reservoir 6 at the desired temperatures above the melting point of the paraffin.

The apparatus also comprises a pump 9 adapted to draw the liquid from one of the three reservoirs 2, 4, 6 and to deliver the liquid to a feed conduit 10 at the inlet side of a distributing means which, in the embodiment illustrated, comprises a flexible hose 12 having a pistol-grip spray nozzle 13 at its free end. An agitator or emulsifier 14 is provided between the discharge side of the pump 9 and the inlet conduit 10 of the distributing means. The unit 14 is designed for emulsifying the paraffin fed to the hose 12.

A four-way valve 15 has a first inlet 26 connected to the reservoir 4 in the portion thereof constituting the decantation tank, i.e. to the relatively pure paraffin in the reservoir 4. A second conduit 27 is connected to the valve 15 and the downwardly sloping bottom of the reservoir 2 containing the pure paraffin. A further duct 28 connects the water reservoir 6 with another port of the valve 15 whose discharge port is connected, in turn, to the intake side of the pump 9.

Thus the four-way valve 15, which is connected along the conduit 10 but ahead of the pump 9, permits communication between one of the three reservoirs 2, 4, 6 and the pump 9 to supply the respective liquid to the distributing means 12, 13.

The aforedescribed elements of the apparatus are, as shown, a unit mounted upon a common support 16 displaceable on casters or rollers 17 along a support surface, e.g. the floor. The upper part of this unit is provided with a platform 18 constituting a bed upon which the subject to be treated can lie in a substantially recumbent or horizontal position for the treatment. The floor of this platform is slightly inclined downwardly toward a drain 19 opening into the receptacle or reservoir 4.

As noted, the latter constitutes a decantation tank provided at its bottom with a filter 20 adapted to separate the paraffin from the water and any detritus formed in the course of treatment. The bottom of this tank, below the filter 20, is inclined downwardly to the left to permit draining of the water and the detritus through a valve 22 in the bottom of the tank.

The hose 12 and the spray gun 13 can be held on a wall 60 of the support 16 by a bracket 61 and a holder 62 in a position of nonuse. The wall 60 can also carry the control board 23 of the apparatus which can be provided with conventional circuitry for regulating the temperatures and for programming the duration of heating for sterilization of the paraffin in reservoir 4.

The reservoirs 2 and 4 can have capacities each of about 120 liters while the water reservoir 6 has a capacity of about 60 liters. Each of these reservoirs if formed as a double wall structure which as shown in FIG. 2, is filled with thermal insulation (e.g. glass wool) deposited between the walls. The reservoir, moreover, can lie inwardly from the outer walls 63 and 64 of the support 16, thereby preventing contact of any heated wall portion with an operator. Each of the reservoirs can also be provided with a temperature indicator as has been represented diagrammatically at 24.

The platform 18 can be swingably mounted by a hinge 65 upon the support 16 to enable it to be swung in the direction represented by arrow 25 for access to the upper parts of the reservoir, e.g. for initial filling and cleaning.

The unit shown in the drawing operates as follows:

In the first stage of operation, the paraffin 5 is pumped via the valve 15, the pump 9 and the emulsifier 14 through the conduit 10 to the hose 12 and the spray gun 13 for application to the body of a subject recumbent upon the platform 18. Excess paraffin passes through the outlet 19 back into the reservoir 4 (see FIG. 3). Since the paraffin has not yet been previously used, it is pure.

Naturally, if the paraffin has been previously used, it is separated from the detritus and water by the filter 20 and is sterilized by control of the temperature in reservoir 4 to a level between 45° and 110° C. During this first phase of operation, the valve 15 is controlled to communicate between the reservoir 4 and duct 26 whose upper end opens above the filter 20 and the inlet conduit 10 has been represented diagrammatically in FIG. 3.

During the second phase of operation, normally used for the treatment of the subject, the pure paraffin from reservoir 2 is fed via the duct 27 and valve 15 through the pump 9 and the emulsifier 14 to the hose 12 as represented diagrammatically in FIG. 4. The paraffin 3 in the tank 2 is held at a temperature sufficient to maintain it in a molten state, generally between 45° and 50° C. The paraffin is applied to the subject at the desired locations by the spray gun 13 whose nozzle permits application of the paraffin in the form of a band having a width of about 100 mm to a thickness determined by the rate at which the spray is traversed over the part.

The third phase of operation, following the treatment of the subject, consists in purging the distribution means. For this purpose, wash water 7 from the reservoir 6 at a temperature of about 90° C. is communicated by valve 15 via the duct 28 to the pump 9 and thence through the emulsifier 14 into the hose 12. This connection path has been represented diagrammatically in FIG. 5.

The wash water can be used to clean the platform 18 to scrub away any detritus which may have accumulated thereon during treatment. The wash water and entrained detritus and paraffin pass through the outlet 19 to the reservoir 4 for decantation and sterilization. The paraffin can be transferred from the reservoir 4 to the reservoir 2 by connecting via valve 15 the ducts 26 and 27.

The apparatus thus simplifies considerably the application of paraffin to the body of a subject and thus permits a more practically and rapid treatment. The apparatus provides in a single unit all of the elements necessary for carrying out the process and permits this apparatus to be moved wherever desired.

I claim:

1. An apparatus for applying paraffin as a treatment agent to the human body, comprising:
   a support;
   means forming a first reservoir on said support for receiving pure treatment agent;
   means forming a second reservoir on said support for the recovery and sterilization of said agent;
   means forming a third reservoir on said support receiving a washing liquid;
   respective heating means associated with each of said reservoirs and heating the contents thereof;
   distributing means on said support for applying said agent to a subject to be treated; a pump on said support means connecting said pump to each of said reservoirs and to said distributing means for feeding said agents and said washing liquid to said distributing means, said distributing means including a flexible hose connected to said pump and a spray gun on said hose; a platform above said reservoirs and mounted on said support for receiving a human body and draining into said second reservoir a four-way valve having respective ports connected to each of said reservoirs and to said distributing means for controlling the flow of said agent and said liquid to said pump; and
   a decantation tank in said second reservoir formed at its bottom with a filter for separation of said agent from said liquid and detritus formed during the treatment of said subject.

2. The apparatus defined in claim 1 wherein said heating means includes means for heating said first reservoir to a temperature of substantially 45° to 50° C. and sufficient to maintain paraffin, as said agent, in a liquid state.

3. The apparatus defined in claim 2 wherein said heating means of said second reservoir is constructed and arranged to maintain a temperature therein sufficient to sterilize paraffin and between 45° and 110° C.

4. The apparatus defined in claim 3, further comprising rollers on said support enabling displacement of the apparatus along a floor.

5. The apparatus defined in claim 4 wherein each of said reservoirs is surrounded by a double wall structure having an insulating material between the walls thereof.

6. The apparatus defined in claim 5 wherein each of said first and second reservoirs has a downwardly inclined bottom, said first reservoir communicating with said valve to the low point of said bottom, the low point of said second reservoir being provided with a drain valve.

7. The apparatus defined in claim 6 wherein said second reservoir is provided with said filter above the bottom of said second reservoir, said valve having a pipe opening into said second reservoir above said filter.

* * * * *